United States Patent [19]

Tóth et al.

[11] Patent Number: 4,593,047

[45] Date of Patent: Jun. 3, 1986

[54] PROCESS FOR THE PREPARATION OF 3-TRIFLUOROMETHYL-AND 2,5-DIMETHYL-4'-HDYROXY-α-ETHYL-BENZHYDROL, AND PHARMACEUTICAL COMPOSITIONS CONTAINING THEM

[75] Inventors: Edit Tóth; József Tórley; György Fekete; László Szporny; László Vereczkey; Éva Palosi; Imre Klebovich; Pál Vittay; Sandor Görög; István Hajdu, all of Budapest, Hungary

[73] Assignee: Richter Gedeon Vegyeszeti Cyar RT, Budapest, Hungary

[21] Appl. No.: 565,835

[22] Filed: Dec. 27, 1983

[30] Foreign Application Priority Data

Dec. 28, 1982 [HU] Hungary ............................ 4186/82

[51] Int. Cl.$^4$ ........................................... A61K 31/065
[52] U.S. Cl. .................................. 514/726; 514/811
[58] Field of Search ................. 424/345; 514/726, 811

[56] References Cited

U.S. PATENT DOCUMENTS 4,094,908 6/1978 Toth et al. ...................... 260/570 R

OTHER PUBLICATIONS

Arzneimittelforschung, 28 (1), 4, 673–677 (1978).
Chem. Abstracts 92:52927b (1980) Szinai et al, Proc. 19th Hung. Ann. Meet, Biochem. 1979.

Primary Examiner—Stanley J. Friedman
Assistant Examiner—John W. Rollins, Jr.
Attorney, Agent, or Firm—Karl F. Ross; Herbert Dubno

[57] ABSTRACT

The invention relates to the preparation of 3-trifluoromethyl- and 2,5-dimethyl-4'-hydroxy-α-ethyl-benzhydrol. Both compounds have so far been described only as metabolites of corresponding benzhydrol derivatives containing no hydroxyl group. Neither their physico-chemical characteristics nor their manufacturing processes have been disclosed in the known publications.

3-Trifluoromethyl- and 2,5-dimethyl-4'-hydroxy-α-ethyl-benzhydrol are suitable for the treatment of acute ethanolic intoxication. Accordingly, another aspect of the invention is a pharmaceutical composition containing one of these compounds as active ingredient.

3 Claims, No Drawings

PROCESS FOR THE PREPARATION OF 3-TRIFLUOROMETHYL-AND 2,5-DIMETHYL-4'-HDYROXY-α-ETHYL-BENZHYDROL, AND PHARMACEUTICAL COMPOSITIONS CONTAINING THEM

The invention relates to the preparation of 3-trifluoromethyl- and 2,5-dimethyl-4'-hydroxy-α-ethyl-benzhydrol. According to another aspect of the invention there are provided pharmaceutical compositions containing these compounds as active ingredient.

3-Trifluoromethyl-4'-hydroxy-α-ethyl-benzhydrol was first described in Arzneimittelforschung, 28 (I), 4, 673–677 (1978), as a metabolite of 3-trifluoromethyl-α-ethyl-benzhydrol which has an inducing effect on the enzyme system of liver. The metabolism of 2,5-dimethyl-α-ethyl-benzhydrol, which shows a similar activity, was studied by Szinai et al. (Proc. 19$^{th}$ Hung. Ann. Meet. Biochem. 1979). The authors concluded that the biotransformation of 2,5-dimethyl-α-ethyl-benzhydrol affords hydroxyl-containing compounds. Neither the physico-chemical characteristics of the mentioned metabolites nor their manufacturing processes are, however, disclosed in any of these publications.

It has now surprisingly been found that 3-trifluoromethyl- and 2,5-dimethyl-4'-hydroxy-α-ethyl-benzhydrol are suitable for the treatment of acute ethanolic intoxication. Acute alcoholic intoxication is characterized by euphoria, general stimulation, ataxia, somnolence, paralytic condition, etc.

The dangers of this toxic disease state are well known and cannot be disregarded, as the intoxicated person is a threat to the public (e.g. driving while intoxicated) and exposes its own health to serious danger. Acute alcoholic intoxication is a substantial risk factor of cerebral ischaemic infarct (Hillbom, M. et al.: Lancet 2, 1181 (1978); Stroke 12, 422 (1981)). At the same time, ethanolic intoxication has no satisfactory antidote. α-Methyl-p-tyrosine has a normalizing effect on locomotoric hyperactivity on mice, in a dose range in which it decreases the spontaneous locomotor activity of animals (Carlsson, A. et al.: Psychopharm., 26, 307 (1972)). Various stimulants (caffeine, amphetamine) decrease the narcotizing effect of alcohol but prolong the motoric incoordination (ataxia) (Wallagsen, H. et al.: Actions of alcohol, Amsterdam, Elsevier, 1970; Rech, R. H. et al.: Ann. N.Y.Acad. Sci. 28, 426 (1976); Todzy, I. et al.: Psychopharm. 59, 243 (1978)). Both alcoholic intoxication and narcosis are shortened by L-cysteine (Sprince, H. et al.: Agents and Actions, 4, 125 (1974); Nagasawa, H. T. et al.: Life Sci., 17, 707 (1975)). The latter compound was used as a reference substance in the alcoholic narcosis period test we carried out.

The effect of the compounds according to the invention on ethanolic narcosis period was tested on Hann.-Wistar rats of both sexes, each weighing 160 to 180 g. The animals were fasted for 16 hours prior to treatment and tests were performed on groups of 10. The animals were treated with various doses of the test compounds orally. One hour after treatment the rats were administered a 3.5 mg./kg. dose of ethanol intraperitoneally, and their narcosis period was measured from the elapse of the righting reflex until a spontaneous correction of the body position. The mean value of the narcosis period and the percentage difference related to the control were calculated. The results are given in Table 1. Abbreviations:

$\bar{x} \pm S.E.$ = mean value ± standard error
n = number of animals

The control group was treated with placebo and a 3.5 mg./kg. dose of ethanol.
Narcosis period of the control:

$87.4 \pm 6.91$ ($\bar{x} \pm S.E.$) min.

A = 3-trifluoromethyl-4'-hydroxy-α-ethyl-benzhydrol

TABLE 1

| Compound | Dose (mg./kg.) | Ethanolic narcosis period (Control ± S.E. %) | n |
| --- | --- | --- | --- |
| A | 40.0 | 53 ± 5.8 | 10 |
|  | 80.0 | 62 ± 5.1 | 10 |
| L-cysteine | 500.0 | 63 ± 4.2 | 10 |
|  | 1000.0 | 66 ± 5.9 | 10 |
| Control | — | 100 ± 7.9 | 10 |

There was examined the effect of a 40.0 mg./kg. dose of the above test compound on the ethanolic narcosis period as a function of the pretreatment-period, following the test procedure described above. The results expressed in %-age of the difference from the control are shown in Table 2.

TABLE 2

| Compound | Pretreatment period (hours) | Narcosis period control | Narcosis period treated | % | n |
| --- | --- | --- | --- | --- | --- |
| A | 0.5 | 87.2 ± 6.23 | 54.1 ± 3.49 | −38 | 10 |
|  | 1.0 | 85.1 ± 4.91 | 45.1 ± 2.30 | −47 | 10 |
|  | 2.0 | 85.5 ± 9.97 | 29.9 ± 5.08 | −65 | 10 |
|  | 3.0 | 83.4 ± 8.46 | 75.1 ± 4.51 | −10 | 10 |

As appears from the results set forth in Tables 1 and 2, the compounds provided by the present invention efficiently shorten the ethanolic narcosis period, their activity is higher than the activity of L-cysteine when administered in a 10-times smaller dose, and a maximum activity is achieved after two hours pretreatment.

The acute toxicity of the compound A was determined on Hann.-Wistar rats of both sexes, each weighing 160 to 180 g. in groups of 10. The animals were administered a single 2000 mg./kg. oral dose of the test compound, and then observed for 14 days. During this period 40% of the animals perished, i.e. the LD$_{50}$ of the compound is over 2000.0 mg./kg.; accordingly, its toxicity is low.

The central nervous activities of the compounds according to the invention were examined with the following methods: electroshock (Swinyard, E. A., Brown, W. C., Goodman, L. S.: J. Pharmacol. Exp. Ther. 106, 319 (1952)), metrazole spasm (Everett, G. M., Richards, R. K.: J. Pharmacol. Exp. Ther. 81, 402 (1944)), thiosemicarbazide spasm (Da Venzo, J. P., Greig, M. E., Cormin, M. A.: Amer. J. Physiol. 201, 833 (1961)), strychnine spasm (Kerley, T. L., Richards, A. G., Begley, R. W., Abreu, B. B., Wesver, L. C.: J.Pharmacol. Exp. Ther. 132, 360 (1961)), nicotine spasm (Stone, C. A., Mecklenburg, K. L., Torhans, M. L.: Arch. Int. Pharmacodyn. 117, 419 (1958)), rotarod test (Kinnard, W. C., Carr, C. J.: J. Pharmacol. Expt. Ther. 121, 354 (1957)), physostigmine lethality preventing effect (Nose, T., Kojima, M.: Europ. J. Pharmacol. 10, 83 (1970)), yohimbine potentiation effect (Quinton, R. M.: Brit. J. Pharmacol. 21, 51 (1963)), and analgesic activity (Bianchi, G., Francheschini, J.: Brit. J. Pharm. Chemother. 9, 280 (1954)). In the above tests the compounds according to the invention proved ineffective even in a dose of 120 mg./kg.

The pharmacologically active compounds according to the invention can be used in therapy in the form of pharmaceutical compositions which are formulated as preparations suitable for oral, rectal and/or parenteral administration. For oral administration tablets, dragées or capsules are prepared. The oral formulations contain as a vehicle e.g. lactose or starch, as an excipient or a granulation aid e.g. gelatine, carboxymethyl cellulose, polyvinyl pyrrolidone or starch gum, as a disintegrating substance e.g. potato starch or microcrystalline cellulose, ultraamylopectin or formaldehyde casein, etc. The formulations may also contain adhesives and lubricants such as talc, colloidal silica, stearin, calcium or magnesium stearate, etc.

Tablets are prepared for example by wet granulation and subsequent pressing. A mixture of the active ingredient and the vehicle and optionally a portion of the disintegrating agent are granulated with an aqueous, alcoholic or aqueous-alcoholic solution of the excipients in a suitable equipment, and the granulate is dried. The remaining portions of the disintegrating substance, lubricant, anti-adhesive or optional further additives are then added to the granules, and the mixture is pressed to tablets. If desired, the tablets are prepared with a dividing line, which facilitates administration. Tablets can be prepared also from a mixture of the active ingredient and suitable additives by direct pressing.

If desired, the tablets can be converted into dragées, using protecting, flavoring agents and pigments generally known for the preparation of pharmaceutical compositions, e.g. sugar, cellulose derivatives (methyl or ethyl cellulose, carboxymethyl cellulose sodium, etc.), polyvinylpyrrolidone, calcium phosphate, calcium carbonate, food pigments, food oil varnishes, aroma substances, iron oxide pigments, etc.

Capsules are prepared by filling a mixture of the active ingredient and the additives into suitable capsules.

For rectal administration the compositions are formulated as suppositories, which contain in addition to the active ingredient a carrier mass, a so-called adeps pro suppository. Suitable carriers include vegetable fats, e.g. hardened vegetable oils, triglycerides of fatty acids having 12 to 18 carbon atoms, preferably Witepsol (a registered trade mark). The active ingredient is homogeneously distributed in the melted carrier mass, and suppositories are prepared by casting.

For parenteral administration injectable preparations are prepared. To prepare an injectable solution the active ingredient is dissolved in distilled water and/or various organic solvents, e.g. glycol ethers, optionally in the presence of dissolution aids, e.g. polyoxyethylene sorbitan monolaurate, monooleate or monostearate (Tween 20, Tween 60, Tween 80). The injectable solutions may contain also various additives, e.g. preserving agents such as benzyl alcohol, p-oxy-benzoic acid methyl or propyl ester, benzalkonium chloride or phenyl mercuri borate, etc., antioxidants such as ascorbic acid, tocopherol, sodium pyrosulfate and optionally complexing agents to bind the metal traces such as ethylene diamine tetraacetate, buffers to adjust the pH and optionally local anaesthetics such as lidocaine. The injectable solutions are filtered, filled into ampoules and sterilized.

The daily dose, depending on the state of the patient, varies between 0.1 and 300.0 mg./kg., preferably 2.0 and 160 mg./kg., preferably administered in more smaller units.

According to the invention 3-trifluoromethyl- and 2,5-dimethyl-4'-hydroxy-α-ethyl-benzhydrol are prepared by (a) reacting 4'-hydroxy-propiophenone with an organometallic compound of the formula (I)

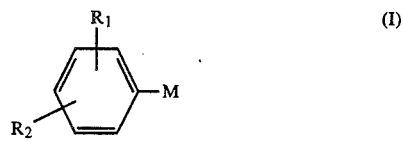

wherein
$R_1$ is hydrogen and
$R_2$ is 3-trifluoromethyl, or
$R_1$ is 2-methyl and
$R_2$ is 5-methyl, and
M represents an alkali metal, preferably lithium, sodium or potassium, or an MgX group, in which X is halogen; or (b) reacting a benzophenone of the formula (II)

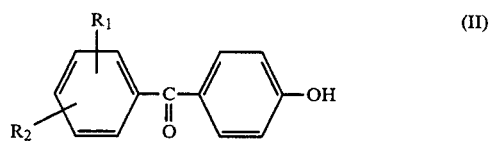

wherein $R_1$ and $R_2$ each have the same meanings as defined above, with an organometallic compound containing an ethyl group, preferably ethyl magnesium halide or ethyl lithium; or (c) reducing a compound of the formula (III)

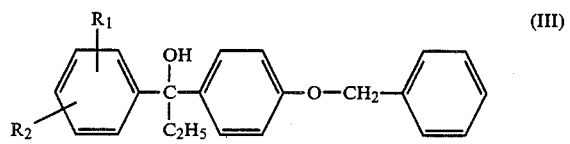

wherein $R_1$ and $R_2$ are as defined above.

The starting compounds are known or can be prepared by methods known in the art.

The starting compounds of the formula (I) can for example be prepared by preparing Grignard reactants from the corresponding substituted aryl halides by known techniques (see e.g. M. S. Kharash et al.: Grignard Reactions of Nonmetallic Substances, Ed., Prentice-Hall. Inc. (1954) pp. 5–90), while the alkali metal-organic compounds can be prepared following the method disclosed in Houben-Weyl: Methoden der Organischen Chemie, XIII/1, pp. 134–159 and 389–405 (1970).

The hydroxy-ketones of the formula (II) can for example be synthesized by Fries reaction (A. H. Blatt: The Fries reaction in organic reactions, Ip, 342). The starting compound of the formula (III) can for example be obtained by reacting 4-benzyloxy-propiophenone with the corresponding substituted phenyl magnesium halides, for example following the method reported by M. S. Kharash et al. (Grignard Reactions of Nonmetallic Substances, Ed., Prentice-Hall Inc. (1954) pp. 138–143).

According to a preferred embodiment of process variant (a), 4-hydroxy-propiophenone is reacted with at least two molar equivalents of an organometallic compound of the formula (I) in a dry inert organic solvent, preferably in inert gas atmosphere. As an organometallic compound preferably appropriately substituted phenyl lithium, more preferably an appropriately substituted phenyl magnesium halide such as chloride or bromide is employed. The reaction is performed in an aprotic organic solvent such as hexamethyl phosphorus amide, dimethyl sulfoxide, aliphatic or cycloalphatic ethers such as diethyl ether, dibutyl ether, ethylene glycol dimethyl ether, dioxane, tetrahydrofurane, aliphatic or aromatic hydrocarbons such as ligroin, benzene, toluene, xylene, or a mixture of these solvents. As an inert gas for example nitrogen or argon is used. The reaction temperature may range from $-70°$ C. up to the boiling point of the solvent, and preferably is between $-40°$ C. and $100°$ C. The product is isolated from the reaction mixture by known techniques. For example, the reaction mixture is decomposed with a dilute aqueous mineral or organic acid, for example with an aqueous solution of sulfuric acid, hydrochloric acid, acetic acid, or preferably with an aqueous ammonium chloride solution, and the product is separated. If desired, the product is purified, e.g. by chromatography or recrystallization.

According to a preferred embodiment of process variant (b) a benzophenone of the formula (II) is reacted with at least two molar equivalents of an ethyl magnesium halide or ethyl lithium, in an inert organic solvent, preferably in inert gas atmosphere. As an ethyl magnesium halide preferably ethyl magnesium iodide or bromide is employed in the reaction. The reaction is continued in the solvent and at temperatures described in connection with process variant (a), for example in nitrogen or argon atmosphere, and the product is isolated as described above.

According to process variant (c) a compound of the formula (III) is reduced. The reductive splitting of benzyl group is preferably carried out by catalytic hydrogenation. As a catalyst metals such as ruthenium, palladium, platinum, nickel, iron, copper, cobalt, chromium, zinc, molybdenum, tungsten, etc. and the oxides and sulfides of these metals are employed. The catalysts may be prepared by reducing their stable oxides with hydrogen, directly in the reaction vessel. This procedure is especially suitable for the preparation of a finely distributed platinum or palladium catalyst. The catalytic hydrogenation may be accomplished also in the presence of catalysts precipitated on the surface of a carrier, e.g. charcoal, silica, alumina or sulfates or carbonates of alkali earth metals. Alternatively, the reduction may be carried out in the presence of a Raney-nickel catalyst. Catalytic hydrogenation is preferably performed in the presence of palladium, in particular palladium-on-charcoal or Raney nickel, in an organic solvent inert under the reaction conditions. As a solvent for example lower aliphatic alcohols, ethers, esters, aliphatic, cycloaliphatic and aromatic hydrocarbons or mixtures of these solvents may be employed. The hydrogenation may be carried out under atmospheric or higher pressure, preferably not exceeding 506.6 kPa, at a temperature between 20° C. and the boiling point of the reaction mixture. The reduction is preferably carried out at room temperature, under atmospheric pressure, until ceasing of the hydrogen uptake. The catalyst is then filtered off and, if desired, the product is purified e.g. by distillation or crystallization.

The invention will further be described with reference to the following illustrative examples.

EXAMPLE 1

3-Trifluoromethyl-4'-hydroxy-α-ethyl-benzhydrol

To a solution of a Grignard reactant prepared from 11 g. of magnesium and 101.3 g. of 3-bromobenzene trifluoride in tetrahydrofurane a solution of 22.5 g. of 4-hydroxy-propiophenone in 405 ml. of tetrahydrofurane is added at 66° to 68° C. The reaction mixture is boiled for an additional hour. The progress of the reaction is monitored by thin layer chromatography. When the reaction is complete, the reaction mixture is cooled to 0° C. and poured onto a mixture of glacial acetic acid and ice. The organic phase is washed to neutral with a saturated sodium chloride solution, dried over sodium sulfate, and the solvent is distilled off under reduced pressure. Recrystallization of the crude product from a mixture of ethyl acetate and n-hexane, after decoloring with activated carbon, yields 30.5 g. of the named compound, melting at 102.5° to 103° C.

Analysis for $C_{16}H_{15}F_3O_2$: Calculated: C 64.86%, H 5.10%, F 19.24%; Found: C 64.89%, H 5.16%, F 18.93%.

EXAMPLE 2

3-Trifluoromethyl-4'-hydroxy-α-ethyl-benzhydrol 54.1 g. of 3-trifluoromethyl-4'-benzyloxy-α-ethyl-benzhydrol in 541 ml. of methanol are hydrogenated under atmospheric pressure, in the presence of 27.1 g. of a 10% palladium-on-charcoal catalyst. When the uptake of the calculated amount of hydrogen is complete, the catalyst is filtered off, and the solvent is distilled off under reduced pressure. The crude product is decoloured with charcoal in ethyl acetate, and recrystallized from a mixture of ethyl acetate and n-hexane. 30.8 g. of the named compound are obtained, melting at 102.5° to 103° C.

Analysis for $C_{16}H_{15}F_3O_2$: Calculated: C 64.86%, H 5.10%, F 19.24%; Found: C 64.72%, H 5.13%, F 19.15%.

EXAMPLE 3

3-Trifluoromethyl-4'-hydroxy-α-ethyl-benzhydrol

To an ethereal solution of ethyl lithium prepared from 4.2 g. of lithium metal and 32.7 g. of ethyl bromide a solution of 20 g. of 3-trifluoromethyl-4'-hydroxy-benzophenone in 100 ml. of dry tetrahydrofurane is added dropwise, with stirring in argon atmosphere, at a temperature between $-30°$ C. and $-40°$ C. The reaction mixture is then allowed to warm up to 0° C., and it is stirred at this temperature for 30 minutes. The reaction mixture is decomposed with a 20% aqueous ammonium chloride solution, under cooling. The aqueous phase is extracted with ether, the ethereal phases are combined and washed to neutral with water. The mixture is dried over anhydrous magnesium sulfate, and the solvent is evaporated under reduced pressure. Crystallization of the residue from a mixture of n-hexane and ethyl acetate yields 9.5 g. of the named compound, melting at 102.5° to 103° C.

Analysis for $C_{16}H_{15}F_3O_2$: Calculated: C 64.86%, H 5.10%, F 19.24%; Found: C 65.01%, H 5.03%, F 19.28%.

Similarly there can be prepared 2,5-dimethyl-4'-hydroxy-α-ethyl-benzhydrol by proper selection of the starting substances. Melting point: 106° to 107° C.

Analysis for $C_{17}H_{20}O_2$: Calculated: C 79.65%, H 7.86%; Found: C 79.80%, H 7.91%.

EXAMPLE 4

The compounds according to the invention can for example be converted into the following pharmaceutical compositions.

Tablets

| Composition of a single tablet: | |
|---|---|
| active ingredient | 100.0 mg. |
| lactose | 184.0 mg. |
| potato starch | 80.0 mg. |
| polyvinyl pyrrolidone | 8.0 mg. |
| talc | 12.0 mg. |
| magnesium stearate | 2.0 mg. |
| aerosil (colloidal $SiO_2$) | 2.0 mg. |
| ultraamylopectin | 12.0 mg. |

From the above ingredient 400-mg. tablets are prepared by wet granulation and subsequent pressing.

Active ingredient: 3-trifluoromethyl-4'-hydroxy-α-ethyl-benzhydrol

Dragées

Tablets as described above are coated with a layer prepared from sugar and talc in a known manner. Dragées are polished with a mixture of bee wax and carnauba wax. Weight of a dragée: 500.0 mg.

Capsules

| Composition of a capsule: | |
|---|---|
| active ingredient | 50.0 mg. |
| lactose | 100.0 mg. |
| talc | 2.0 mg. |
| potato starch | 30.0 mg. |
| cellulose (microcrystalline) | 8.0 mg. |

The active ingredient is thoroughly admixed with the additives, the mixture is passed through a 0.32-mm. sieve, and filled into No. 4 hard gelatine capsules.

Active ingredient: 3-trifluoromethyl-4'-hydroxy-α-ethyl-benzhydrol

Suppositories

| Composition of a suppository: | |
|---|---|
| active ingredient | 100.0 mg. |

| Composition of a suppository: | |
|---|---|
| lactose | 200.0 mg. |
| basic substance of suppository (e.g. Witepsol H) | 1700.0 mg. |

The basic substance is melted and then cooled to 35° C. The active ingredient is thoroughly admixed with the lactose, and the mixture is homogenized in the basic substance with a suitable equipment. The obtained mass is filled into cool molds. One suppository weights 2000 mg.

Active ingredient: 3-trifluoromethyl-4'-hydroxy-α-ethyl-benzhydrol.

Suspension

| Composition of 100 ml. of suspension: | |
|---|---|
| active ingredient | 1.0 g. |
| sodium hydroxide | 0.26 g. |
| citric acid | 0.30 g. |
| nipagin (4-hydroxy-benzoic acid methyl ester sodium salt) | 0.10 g. |
| Carbopol 940 (polyacrylic acid) | 0.30 g. |
| ethanol (96%) | 1.00 g. |
| raspberry aroma | 0.60 g. |
| sorbite (70% aqueous solution) | 72.00 g. |
| distilled water up to | 100.00 ml. |

To a solution of nipagin and citric acid in 20 ml. of distilled water Carbopol is added in small portions, with vigorous stirring, and the solution is allowed to stand for 10 to 12 hours. Thereafter a solution of the above amount of sodium hydroxide in 1 ml. of distilled water is added dropwise, followed by dropwise addition of an aqueous solution of sorbite and an ethanolic raspberry aroma solution, with stirring. Active ingredient is then added in small portions, and the mixture is homogenized. The suspension is supplemented with distilled water ad 100 ml., and the suspension syrup is passed through a colloidal mill.

Active ingredient: 3-trifluoromethyl-4'-hydroxy-α-ethyl-benzhydrol.

We claim:

1. A method of treating acute ethanolic intoxication in an affected animal subject which comprises administering to the subject a pharmacologically effective amount of 3-trifluoromethyl-4'-hydroxy-α-ethylbenzhydrol.

2. The method of treating acute ethanolic intoxication in an affected animal subject as defined in claim 1 wherein the 3-trifluoromethyl-4'-hydroxy-alpha-benzhydrol is administered orally, rectally or parenterally.

3. The method of treating acute ethanolic intoxication in an affected animal subject as defined in claim 1 wherein the daily dosage is 0.1 to 300 mg/kg.

* * * * *